(12) United States Patent
Meyer et al.

(10) Patent No.: US 6,789,940 B2
(45) Date of Patent: Sep. 14, 2004

(54) MEDICAL X-RAY EXAMINATION DEVICE

(75) Inventors: Michael Meyer, Hausen (DE); Peter Soukal, Schwarzenbruck (DE)

(73) Assignee: Siemens Aktiengesellschaft, München (DE)

( * ) Notice: Subject to any disclaimer, the term of this patent is extended or adjusted under 35 U.S.C. 154(b) by 3 days.

(21) Appl. No.: 10/224,953

(22) Filed: Aug. 21, 2002

(65) Prior Publication Data

US 2003/0053599 A1 Mar. 20, 2003

(30) Foreign Application Priority Data

Aug. 21, 2001  (DE) ......................................... 101 40 862

(51) Int. Cl.⁷ ............................................... H05G 1/02
(52) U.S. Cl. .................................................... 378/196
(58) Field of Search ................................ 378/195–198

(56) References Cited

U.S. PATENT DOCUMENTS

| | | |
|---|---|---|
| 5,386,453 A | 1/1995 | Harrawood et al. |
| 5,822,814 A | 10/1998 | Van der Ende |
| 5,870,450 A * | 2/1999 | Khutoryansky et al. .... 378/197 |
| 6,220,752 B1 | 4/2001 | Csikos et al. |
| 6,364,525 B1 * | 4/2002 | Mellstrom et al. .......... 378/197 |

FOREIGN PATENT DOCUMENTS

| | | |
|---|---|---|
| DE | OS 199 27 480 | 1/2001 |
| EP | 0 877 538 | 11/1998 |

* cited by examiner

Primary Examiner—Craig E. Church
(74) Attorney, Agent, or Firm—Schiff Hardin LLP

(57) ABSTRACT

A multi-functional X-ray examination has a base, a guide rail attached to the base and two trucks that are attached to the guide rail and are movable along the guide rail. An X-ray exposure system is movable in the longitudinal direction with the first truck, and a patient support mechanism is movable in the longitudinal direction with the second truck. The two trucks can be driven along the guide rail independently of one another.

9 Claims, 3 Drawing Sheets

MEDICAL X-RAY EXAMINATION DEVICE

BACKGROUND OF THE INVENTION

1. Field of the Invention

The present invention is directed to a medical X-ray examination device of the type having a base, a guide rail attached to the base, a first truck attached to the guide rail and movable along the guide rail, an X-ray exposure system attached to the first truck, and a patient support mechanism.

2. Description of the Prior Art

German OS 198 49 091 discloses an X-ray examination device with two trucks to which a transillumination image converter and an exposure image converter are attached, respectively.

German OS 99 27 480, U.S. Pat. Nos. 5,386,453 and 5,822,814 and European Application 0 877 538 disclose multi-functional X-ray diagnostic devices which allow a number of different X-ray examinations to be implemented. The devices disclosed by German OS 199 27 480, U.S. Pat. No. 5,822,814 and European Application 0 877 538 have a base to which a horizontal guide rail is attached and a truck attached to and movable along the guide rail, an X-ray exposure system being attached to the truck. The X-ray exposure system according to U.S. Pat. No. 5,822,814 and European Application 0 877 538 is implemented with a C-arm with opposite ends at which an X-ray radiator and an X-ray detector are arranged, respectively. A large region of the patient lying on a patient bearing mechanism can be reached with the X-ray exposure system by means of the truck movable along the guide rail.

According to an embodiment in European Application 0 877 538, the patient support mechanism is attached to the same truck and is longitudinally displaceable together with the X-ray exposure system.

In the known X-ray diagnostic systems, the number of possible X-ray examinations is limited or some X-ray examinations are possible only using a less user-friendly operating mode.

SUMMARY OF THE INVENTION

An object of the present invention is to provide a multi-functional X-ray diagnostic device of the type initially described wherein the number of possible X-ray examinations is increased and the user-friendliness and accessibility to the patient by attenuating personnel are improved.

This object is achieved in accordance with the invention in an X-ray examination device of the type initially described which additionally has a second truck attached to the guide rail and movable along the guide rail, the patient support mechanism being attached to this second truck via a boom.

As used herein "truck" means any element movable along a guide rail, for example a carriage or a rider. The X-ray exposure system contains, for example, image-generating components such as an X-ray tube, and X-ray film or some other X-ray detector in the X-ray examination device, particularly an imaging X-ray examination device.

In the X-ray examination device of the invention, the X-ray exposure system as well as the patient support mechanism with a patient bed can be displaced in the longitudinal direction. For a specific examination, thus, the operating personnel are free to decide whether the X-ray exposure system or the patient bearing mechanism is displaced. For angiography examinations, for example, it is standard and desirable to move the patient support table into the proper position. For an examination in the abdominal/intestinal region, by contrast, it is desirable to adjust the X-ray exposure system in longitudinal direction. Both types of positioning are possible with the X-ray examination device of the invention, so that a greater number of examinations is possible and the user-friendliness is enhanced for the personnel. The multi-functionality is thus improved.

The base is preferably height-adjustable.

The two trucks preferably are driven independently of one another. To this end, a first drive device for moving the first truck and a second drive device for moving the second truck are present, the drive devices being implemented such that the two trucks can be driven independently of one another.

In a preferred version, a stationary spindle with a first spindle nut and with a second spindle nut is provided for realizing the independent drives, the first drive device being a first drive motor arranged at the first truck for driving the first spindle nut, and the second drive device being a second drive motor arranged at the second truck for driving the second spindle nut.

In another preferred version, two spindles that are respectively driven by separate drive motors are employed. Thus, the first drive device has a first drive motor for driving a first spindle acting on the first truck, and the second drive device has a second drive motor for driving a second spindle acting on the second truck. Respective spindle nuts are arranged in the first and second trucks.

According to a preferred development of the multi-functional X-ray examination device, the guide rail is secured to be base so as to be rotatable around a horizontal axis. The guide rail preferably is rotatable by ±90° relative to the horizontal. The rotatability assures that examinations can also be carried at a standing patient. As a result, the number of possible X-ray examinations, i.e. the multi-functionality, is advantageously enhanced even further.

There are limits placed on the length of the guide rail since the X-ray device would occupy a large space—which often is not present—in the examination room given a longer guide rail. Particularly for a guide rail rotated by ±90°, i.e. for a standing examination of the patient, the height of the room places limits on the length of the guide rail.

A range of displacement of the second truck at the guide rail is preferably greater than 1.0 m, particularly greater than 1.2 m.

According to a preferred embodiment of the X-ray examination device, the X-ray exposure system has a C-arm with opposite ends an X-ray radiator and an X-ray detector are arranged. As a result, the number of possible X-ray examinations is advantageously enhanced even further. For a prone patient, thus, above-table examinations, i.e. examinations with the X-ray radiator arranged above the patient, as well as below-table examinations, i.e. examinations with the X-ray radiator arranged under the patient bed, are possible.

The X-ray exposure system equipped with a C-arm is also particularly advantageous for angiography examinations.

According to another preferred embodiment, the boom can be extended in telescoping fashion.

According to an especially preferred embodiment, the X-ray examination device has an operating handle for moving a support plate of the patient support mechanism, with a force sensor arranged at the operating handle, which supplies a force-proportional electrical output signal to a control unit that generates a force-dependent control signal for a drive motor acting on the support plate. Independently of the motion of the support plate, this embodiment also can be employed in other drive systems wherein an arbitrary object should be capable of being driven by a motor and should also be capable of being moved relatively freely by an operator. For example, it is thus possible for the operator to simulate a floating support plate or tabletop—particularly for angiographic examinations—, i.e. a support plate that is only borne in or on a roller or slide system in the horizontal plane, without having to be coupled to a motor. In accordance with the invention, this operating possibility is enhanced by a force-sensitive or acceleration-sensitive operating handle. The control unit and the drive motor convert the force that the operator exerts on the operating handle into an actual acceleration of the support plate.

DESCRIPTION OF THE PREFERRED EMBODIMENTS

Figure 1:
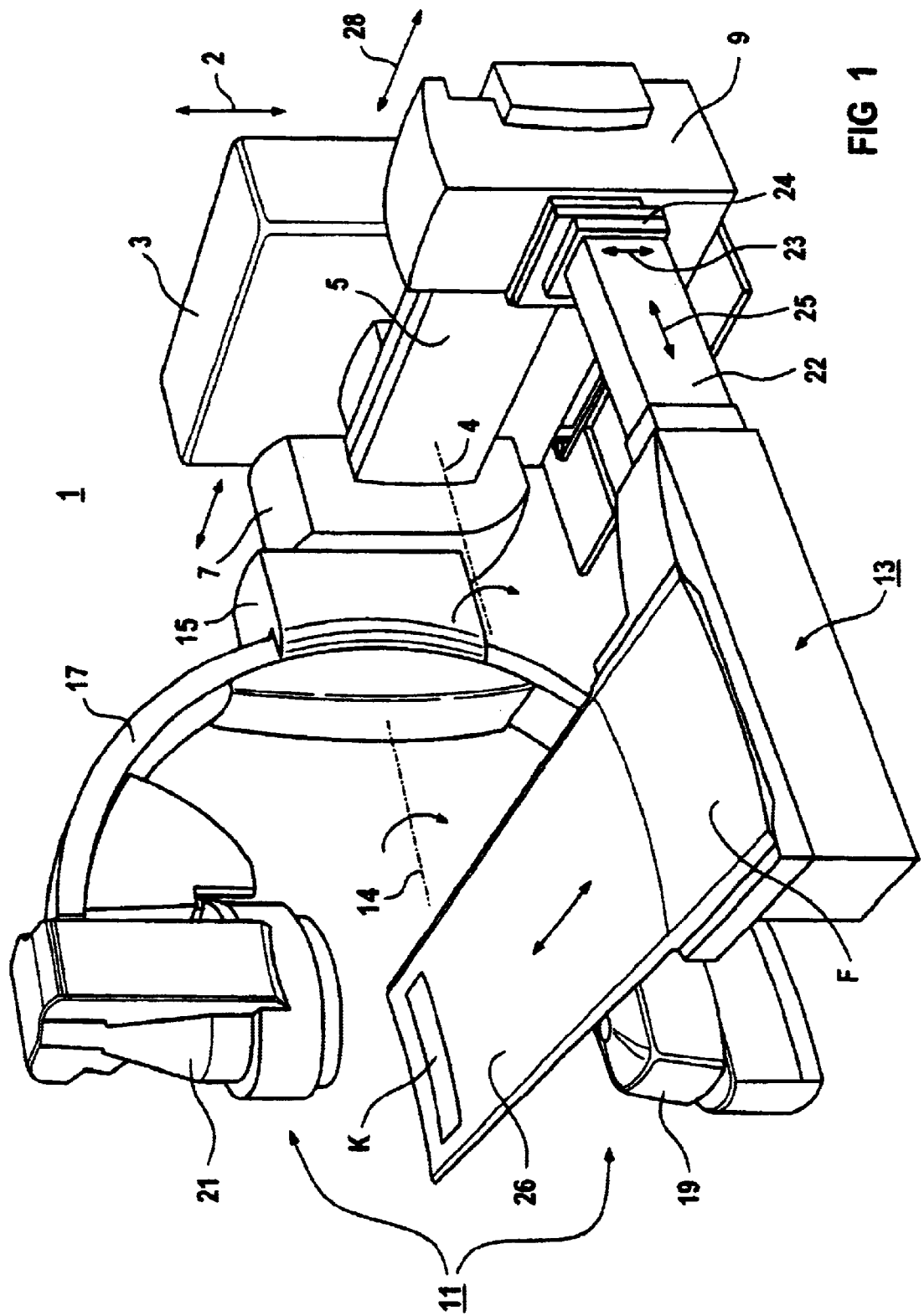
FIG. 1 shows an X-ray examination device of the invention in a perspective view.

FIG. 1 shows an X-ray examination device 1 that stands on the floor of an examination room via a base 3 that is height-adjustable along the arrow 2. A guide rail 5 that is rotatable by ±90° relative to the illustrated, horizontal attitude is seated at the base 3. A clamp-like, first rider or truck 7 and a clamp-like, second rider or truck 9 are movably secured to the guide rail 5.

The first truck 7 carries an X-ray exposure system referenced 11 overall; the second truck 9 carries a patient support mechanism referenced 13 overall.

The X-ray exposure system 11 has a guide element 15 at the first truck 7 that is seated at the first truck 7 so as to be rotatable around a horizontal axis 14. The guide element 15 has a circularly curved guide for the acceptance of a C-arm 17 at its side facing away from the truck 7. The C-arm 17 can execute an arcuate motion in the guide element 15, so that a vertical as well as a horizontal transirradiation of the patient are possible. In the illustrated example, the C-arm 17 carries an X-ray radiator 19 at its lower end and an X-ray detector 21, particularly an image receiver or an image intensifier, at the upper end.

The patient support mechanism 13 has a boom 22 that is secured to a base 24 that is seated at the second truck 9 so as to be height-adjustable in the arrow direction 23. A support plate 26 for the patient (head side K, foot end F given a patient of normal height, approximately 1.90 m) is attached toward one side at the end of the boom 22 that is extensible in telescoping fashion in the arrow direction 25. The telescoping extension of the boom 22 produces a transverse movement of the support plate 26, and the displaceability of the second truck 9 along the guide rail 5 (arrow direction 28) allows longitudinal displacement. A patient can be displaced completely at that side of the boom 22 (between K and F) facing toward the X-ray exposure system 11.

Figure 2:
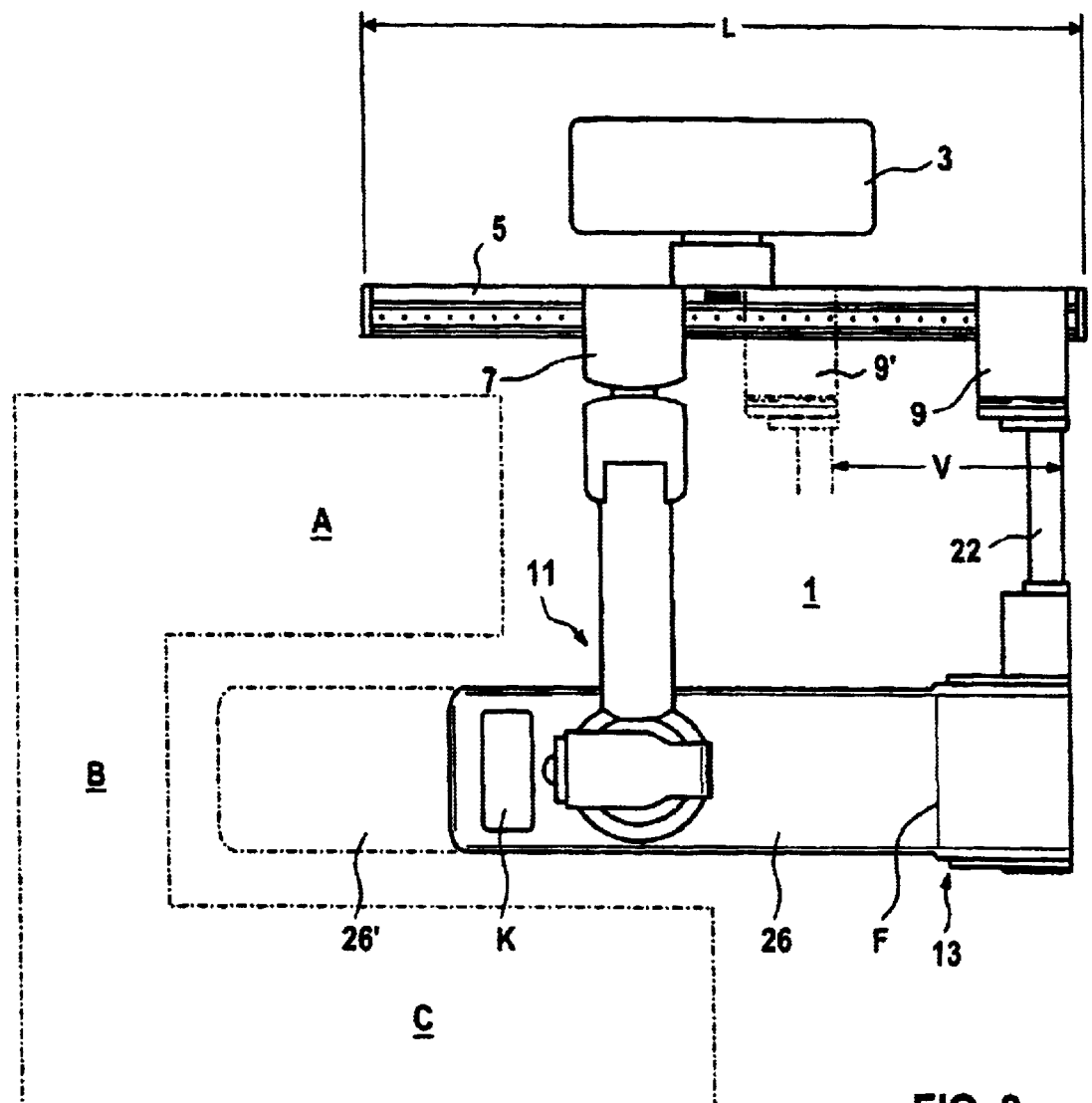
FIG. 2 shows the X-ray examination device of FIG. 1 in a plan view.

FIG. 2 shows the X-ray examination device 1 of FIG. 1 in a plan view. The length L of the guide rail amounts to approximately 2500 through 3000 mm in this example. A displacement range V of the second truck 9 amounts to approximately 1200 mm.

In the position of the second truck 9' shown with broken lines, the support plate 26' is easily accessible from three sides, i.e. in the areas A, B, C. In area A, in particular, operating personnel are not impeded, or only minimally impeded, toward the back by the rail 5. According to a version that is not shown, both trucks 7 and 9 can be moved farther toward the end of the guide rail 5, so that the accessibility is improved even more.

Figure 3:
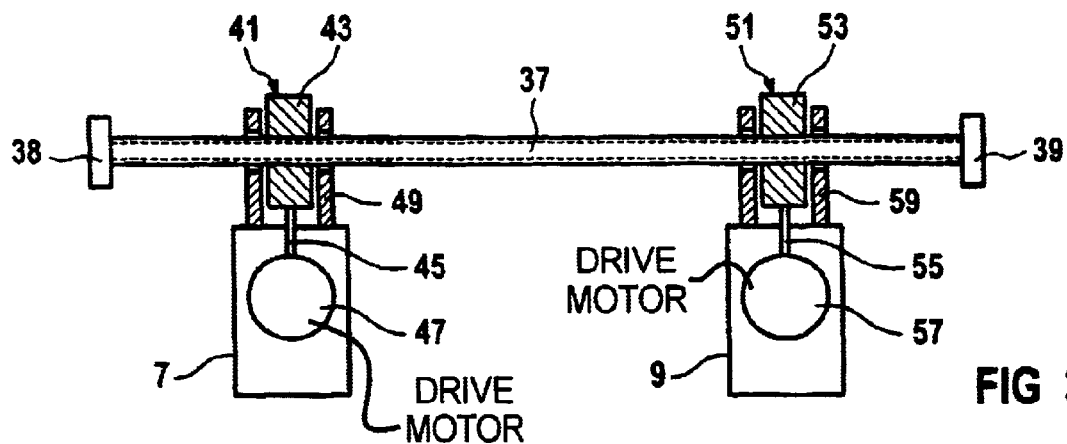
FIG. 3 illustrates a first version of a drive system for the X-ray examination device of FIGS. 1 and 2.
Figure 4:
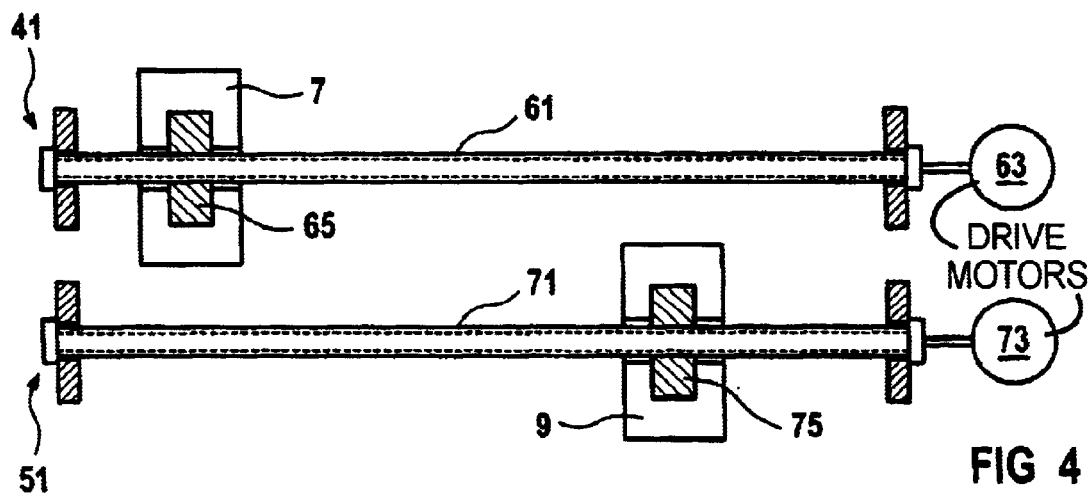
FIG. 4 illustrates a second version of a drive system for the X-ray examination device of FIGS. 1 and 2.

FIGS. 3 and 4 schematically show two different versions for the mutually independent drive of the two trucks 7 and 9 of the X-ray examination device 1. These drive systems are essentially arranged in the inside of the cuboid guide rail 5 and thus cannot be seen in FIG. 1.

According to the version shown in FIG. 3, a common (shared), stationary spindle 37 is present that is fixed in bearings 38, 39 that can be secured at the inside of the guide rail 5. A first drive device 41 is provided for moving the first truck 7, the device 41 having a first spindle nut 43 that can be driven by a drive train 45 (gearwheel, chain, etc.) that is only schematically indicated. To this end, the drive train 45 is in communication with a first drive motor 47 that is arranged in the first truck 7. The first spindle nut 43 is rotatably suspended in a pincers-like bearing support 49 that is in communication with the first truck 7. A second drive device 51 is similarly present for moving the second truck 9. The device 51 having a second spindle nut 53, a drive train 55, a second drive motor 57 and a bearing support 59. The two trucks 7 and 9 can be moved independently of one another by separate operation of the drive motors 47 and 57.

In the alternative design according to FIG. 4, a rotatably seated first spindle 61 as well as a rotatably seated second spindle 71 are present. For example, the spindles 61, 71 are rotatably suspended in the inside of the guide rail 5. A first drive motor 63 that drives the first spindle 61 and a second drive motor 73 that drives the second spindly 71 also are present in the interior of the guide rail 5. Respective spindle nuts 65 and 75 are stationarily secured in the two trucks 7, 9. The trucks 7 and 9 can be moved along the guide rail 5 independently of one another by separate operation of the motors 63 and 73.

Figure 5:
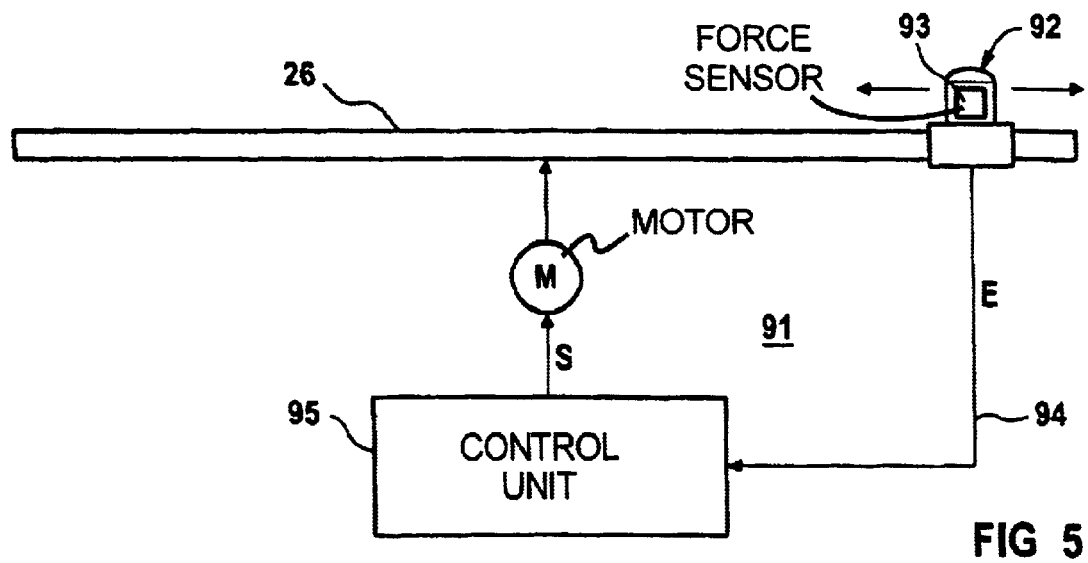
FIG. 5 is a schematic illustration of a table drive control system for the operation of the patient support mechanism of the X-ray examination device of FIGS. 1 and 2.

FIG. 5 schematically shows a table drive control system 91 with which an operator can simulate a freely movable support plate 26—despite a coupling of the patient support mechanism 13 to the second drive device 51. This is advantageous particularly for angiographic examinations since—as already mentioned—an adjustment of the patient support mechanism 13 and, to a lesser extent, a longitudinal displacement of the X-ray exposure system 11 are advantageous and desired.

The table drive control system 91 has an operating handle 92 rigidly connected to the support plate 26, a force sensor 93 being attached to the handle 92 in the gripping region. For example, the force sensor 93 can be a piezoelectric sensor, a wire strain gauge (WSG) or an acceleration sensor. The force sensor 93 generates an electrical signal E that is proportional to the force exerted by the operator. The electrical signal E is supplied via a line 94 to a control unit 95 that generates a control signal S, supplied to a drive motor M, from the force-proportional electrical signal E using a motion model stored in the drive unit 95. For example, the drive motor M (or multiple motors) produce a longitudinal displacement of the bearing plate 26 and/or an optional transverse displacement. A number of force sensors for different force directions can potentially be present for this purpose, at the same operating handle 92.

The motor M accelerates the support plate 26, for example dependent on the force the operator exerts on the operating handle 92. Dependent on whether one or more force sensors are present, the force can be simulated only in terms of magnitude or also according to its direction.

The motion model stored in the control unit 95 can either be conventionally constructed as computer model wherein—as in the case of a manual table or plate motion—a motor control is derived from the exerted force that causes an acceleration, and from the static friction and sliding friction that oppose it. Alternatively, the motion model can be implemented in the form of a fuzzy control wherein motion parameters are empirically optimized in order to come as close as possible to the simulation of a manual table movement.

The table drive control system 91 also can simulate a step-up or step-down, for example in order to achieve the movement of the heavy support plate 26 with little exertion of force. This also facilitates work by the personnel.

In addition to the versatile functionality that has already been described, the X-ray examination device of the invention also has the advantage that a displaceability of the patient is achieved over the entire torso region. The X-ray examination device also allows great accessibility for the medical personnel, i.e. the personnel can access the patient from a great number of sides, for example from the left, from the right and proceeding from the head side, which is particularly significant for emergency operations.

Although modifications and changes may be suggested by those skilled in the art, it is the intention of the inventors to embody within the patent warranted hereon all changes and modifications as reasonably and properly come within the scope of their contribution to the art.

What is claimed is:

1. A medical X-ray examination device comprising:
   a base;
   a guide rail attached to said base;
   a first truck mounted on and movable along said guide rail;
   an X-ray exposure system attached to said first truck;
   a second truck mounted on and movable along said guide rail;
   a patient support mechanism adapted to support a patient for obtaining an X-ray exposure with said X-ray exposure system; and
   a telescoping boom attaching said patient support mechanism to said second truck.

2. A medical X-ray examination device as claimed in claim 1 comprising a first drive device in mechanical engagement with said first truck for moving said first truck, a second drive device in mechanical engagement with said second truck for moving said second truck, said first drive device and said second drive device being operable to move said first and second trucks independently of each other.

3. A medical X-ray examination device as claimed in claim 2 further comprising a stationary threaded spindle having a first spindle nut thereon and a second spindle nut thereon, and wherein said first drive device comprises a first drive motor disposed at said first truck for rotating said first spindle nut to cause movement of said first truck along said stationary spindle, and wherein said second drive device comprises a second drive motor disposed at said second truck for rotating said second spindle nut on said stationary spindle to cause movement of said second truck along said stationary spindle.

4. A medical X-ray examination device as claimed in claim 2 wherein said first drive device comprises a first drive motor and a first spindle in threaded engagement with said first truck, said first drive motor rotating said first drive spindle to cause movement of said first truck along said first spindle, and wherein said second drive device comprises a second drive motor and a second spindle in threaded engagement with said second truck, said second drive motor rotating said second spindle to cause movement of said second truck along said second spindle.

5. A medical X-ray examination device as claimed in claim 1 wherein said guide rail is mounted to said base so as to be rotatable around a horizontal axis.

6. A medical X-ray examination device as claimed in claim 1 wherein said second truck has a range of displacement at said guide rail that is greater than 1.0 m.

7. A medical X-ray examination device as claimed in claim 6 wherein said range of displacement is greater than 1.2 m.

8. A medical X-ray examination device as claimed in claim 1 wherein said X-ray exposure system comprises a C-arm having a first end and a second end, and an X-ray radiator mounted at said first end and an X-ray detector mounted at said second end.

9. A medical X-ray examination device as claimed in claim 1 wherein said patient support mechanism has a support plate movable by an operating handle, and comprising a force sensor disposed at said operating handle which generates a force-proportional electrical output signal in response to a force acting on said handle, and a control unit supplied with said output signal which generates a force-dependent control signal, and a drive motor in driving engagement with said support plate for accelerating said support plate in response to said control signal.

* * * * *